(12) United States Patent
Stroefer et al.

(10) Patent No.: US 7,390,932 B2
(45) Date of Patent: Jun. 24, 2008

(54) METHOD FOR PREPARING HIGHLY CONCENTRATED, GASEOUS FORMALDEHYDES

(75) Inventors: Eckard Stroefer, Mannheim (DE); Neven Lang, Mannheim (DE); Ulrich Steinbrenner, Neustadt (DE); Hans Hasse, Kaiserslautern (DE); Michael Ott, Neckargemünd (DE); Thomas Grützner, Stuttgart (DE)

(73) Assignee: BASF Aktiengesellschaft (DE)

( * ) Notice: Subject to any disclaimer, the term of this patent is extended or adjusted under 35 U.S.C. 154(b) by 356 days.

(21) Appl. No.: 10/547,440

(22) PCT Filed: Mar. 3, 2004

(86) PCT No.: PCT/EP2004/002121

§ 371 (c)(1), (2), (4) Date: Aug. 26, 2005

(87) PCT Pub. No.: WO2004/078690

PCT Pub. Date: Sep. 16, 2004

(65) Prior Publication Data

US 2006/0185513 A1    Aug. 24, 2006

(30) Foreign Application Priority Data

Mar. 4, 2003   (DE) ............................. 103 09 288

(51) Int. Cl.
C07C 45/78 (2006.01)

(52) U.S. Cl. ....................................... 568/470; 568/493

(58) Field of Classification Search .................. None
See application file for complete search history.

(56) References Cited

U.S. PATENT DOCUMENTS

| | | | |
|---|---|---|---|
| 4,472,558 A | 9/1984 | Casper et al. | |
| 6,232,507 B1 | 5/2001 | Kaiser et al. | |
| 6,414,196 B1 | 7/2002 | Sievers et al. | |
| 6,610,888 B1 | 8/2003 | Strofer et al. | |
| 2002/0193639 A1 | 12/2002 | Sievers et al. | |

FOREIGN PATENT DOCUMENTS

| | | |
|---|---|---|
| AT | 252913 | 7/1966 |
| DE | 27 19 967 | 11/1978 |
| DE | 41 37 846 | 5/1993 |
| DE | 198 10 087 | 9/1999 |
| DE | 198 22 598 | 11/1999 |
| DE | 199 10 145 | 8/2000 |
| EP | 1 063 221 | 12/2000 |
| FR | 2 492 367 | 4/1982 |
| GB | 1190682 | 5/1970 |
| WO | WO-99/21818 | 5/1999 |

*Primary Examiner*—Sikarl A Witherspoon
(74) *Attorney, Agent, or Firm*—Connolly Bove Lodge & Hutz LLP

(57) ABSTRACT

Process for preparing high-concentration gaseous formaldehyde having a molar $CH_2O:H_2O$ ratio of $\geq 0.6$ from an aqueous formaldehyde solution by evaporation of at least part of the solution, in which the aqueous formaldehyde solution is heated to a vaporization temperature T and the gas phase formed is taken off, wherein the evaporation temperature T obeys the relationship:

$$T[°C.] \geq T'_{min}[°C.]$$

where $T'_{min}(c) = A + B \times (c/100) + C \times (c/100)^2 + D \times (c/100)^3$
and
$A = +68.759$, $B = +124.77$, $C = -12.851$, $D = -10.095$,
where c is the instantaneous $CH_2O$ content of the aqueous formaldehyde solution during the evaporation in percent by weight and is from 20 to 99% by weight.

15 Claims, 1 Drawing Sheet

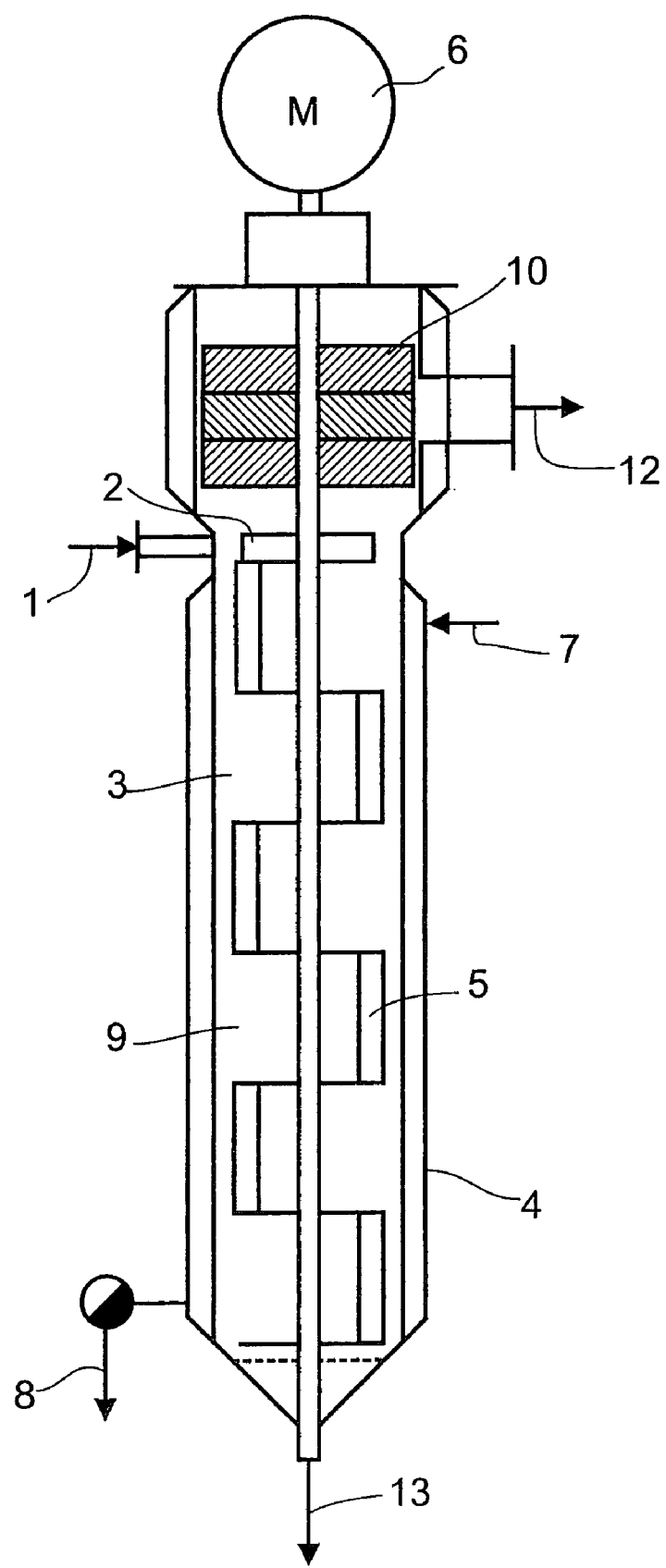

METHOD FOR PREPARING HIGHLY CONCENTRATED, GASEOUS FORMALDEHYDES

RELATED APPLICATIONS

This application is a national stage application (under 35 U.S.C. 371) of PCT/EP2004/002121 filed Mar. 3, 2004 which claims benefit to German application 103 09 228.9 filed Mar. 4, 2003.

The present invention relates to a process for preparing high-concentration gaseous formaldehyde.

Formaldehyde is an important industrial chemical and is used to produce numerous industrial products and consumer articles. Over 50 branches of industry at present make use of formaldehyde, essentially in the form of aqueous solutions or formaldehyde-containing synthetic resins. Commercially available aqueous formaldehyde solutions have total concentrations of from 20 to 55% by weight of formaldehyde in the form of monomeric formaldehyde, methylene glycol and oligomeric polyoxymethylene glycols.

Water, monomeric (free) formaldehyde, methylene glycol and oligomeric polyoxymethylene glycols having various chain lengths are present together in aqueous solutions in a thermodynamic equilibrium which is characterized by a particular distribution of polyoxymethylene glycols of differing lengths. The term "aqueous formaldehyde solution" also refers to formaldehyde solutions in which virtually no free water is present and water is present essentially only in chemically bound form as methylene glycol or in the terminal OH groups of the polyoxymethylene glycols. This is particularly true of concentrated formaldehyde solutions. Polyoxymethylene glycols can have, for example, from 2 to 9 oxymethylene units. Thus, dioxymethylene glycol, trioxymethylene glycol, tetraoxymethylene glycol, pentaoxymethylene glycol, hexaoxymethylene glycol, heptaoxymethylene glycol, octaoxymethylene glycol and nonaoxymethylene glycol can be present together in aqueous formaldehyde solutions. The distribution is concentration-dependent. Thus, the maximum of the distribution in dilute formaldehyde solutions corresponds to homologues having a short chain length, while in more concentrated formaldehyde solutions it corresponds to homologues having a greater chain length. A shift in the equilibrium toward longer-chain (higher molecular weight) polyoxymethylene glycols can be brought about by removal of water, for example by simple distillation in a film evaporator. The establishment of equilibrium in this case occurs at a finite rate by intermolecular condensation of methylene glycol and low molecular weight polyoxymethylene glycols with elimination of water to form higher molecular weight polyoxymethylene glycols.

The use of gaseous formaldehyde is advantageous in many cases. In the gaseous state, formaldehyde is present predominantly in its highly reactive monomeric form. Gaseous mixtures which are substantially free of water and hydroxy compounds can be used in reactions where the latter would interfere, since they lead, for example, to secondary reactions or reduce the selectivity or even deactivate the catalyst, for example in the case of catalysis by Lewis acids. It is frequently also advantageous to carry out reactions as multiphase reactions with participation of a gas phase. There is therefore a need for processes for preparing gaseous formaldehyde/water mixtures having a high formaldehyde/$H_2O$ ratio.

Gaseous formaldehyde can be prepared on the laboratory scale by heating paraformaldehyde. However, the use of paraformaldehyde requires elaborate equipment for handling solids. Paraformaldehyde is therefore not employed on an industrial scale.

The preparation of gaseous formaldehyde by preparation of hemiacetals of formaldehydes and subsequent dissociation of the hemiacetals into alcohol and free formaldehyde is also known. Such a process is described, for example, in DE-A 41 37 846. It requires an extraction step in which formaldehyde is extracted as hemiacetal from an aqueous formalin solution. The hemiacetal obtained is dried and subsequently dissociated thermally into formaldehyde and the alcohol, with the alcohol being separated off and returned to the extraction step. This process is complicated. Furthermore, the alcohol is introduced into the process as a further material. This is expensive and can lead to contamination of the formaldehyde with the alcohol.

Heterogeneously catalyzed, oxidative dehydrogenation of methane likewise gives, as described in DE-A 199 10 145, a formaldehyde/water mixture as reaction product. Since large amounts of fresh water have to be added to the feed gas stream to avoid deactivation of the catalyst, this process does not solve the problem of preparing gas mixtures having a high formaldehyde/water ratio.

The nonoxidative dehydrogenation of methanol to form formaldehyde and hydrogen has been examined intensively in recent times and is described, for example, in DE-A 198 10 087 and DE-A 198 22 598. This process departs from the classic route of oxidative dehydrogenation of methanol to form aqueous formaldehyde solutions. Gaseous methanol is dehydrogenated over a catalyst present in the form of an aerosol. The reaction is endothermic and has to be carried out at high temperatures to achieve a high conversion because of its thermodynamic limitation. However, high to complete conversion of the methanol is necessary for the process to be economical and to prevent formation of hemiacetals and acetals from formaldehyde and unreacted methanol. The high operating temperatures incur high capital costs and energy costs.

The alcohol bound in the acetal can interfere in subsequent reactions of the formaldehyde. The separation of the aerosol catalyst from the product gas is also complicated. However, this separation has to be very complete if the aerosol catalyst deactivates the catalysts which catalyze the subsequent reactions of formaldehyde. Finally, part of the methanol decomposes into CO and hydrogen at the high temperatures of the nonoxidative dehydrogenation of methanol.

It is therefore advisable to adhere to the classical process of oxidative dehydrogenation of methanol. This process has proven itself, is technically mature and has been continually improved. It forms formaldehyde with a selectivity of >90%.

Gaseous formaldehyde can be isolated from the aqueous formaldehyde solution obtained in the classical oxidative dehydrogenation of methanol. While the liquid phase has the above-described distribution of polyoxymethylene glycols of differing chain lengths, formaldehyde is present in the gas phase of methylene glycol $CH_2(OH)_2$ and free formaldehyde $CH_2O$. For example, if a 30% strength by weight aqueous formaldehyde solution is heated to 107° C. or above, a gaseous formaldehyde/water mixture whose formaldehyde content, calculated as $CH_2O$, is from 25 to 35% by weight can be taken off. This corresponds to a molar ratio of $CH_2O$ to water ($CH_2O:H_2O$) of from 0.2 to 0.32.

However, the evaporation of an aqueous formaldehyde solution leads, in the case of highly concentrated formaldehyde solutions, to the precipitation of solids. For example, if a formaldehyde solution having a $CH_2O$ content of 70% by weight is placed in a round-bottom flask and an attempt is made to evaporate it at ambient pressure, precipitation of solids occurs after vaporization of a certain amount of liquid.

It is an object of the present invention to provide an economical process for preparing high-concentration gaseous formaldehyde having a molar $CH_2O:H_2O$ ratio of $\geq 0.6$.

We have found that this object is achieved by a process for preparing high-concentration gaseous formaldehyde having a molar $CH_2O:H_2O$ ratio of $\geq 0.6$ from an aqueous formaldehyde solution by evaporation of at least part of this solution, in which the aqueous formaldehyde solution is heated to an evaporation temperature T and the gas phase formed is taken off, wherein the evaporation temperature T obeys the relationship:

$$T[°C.] \geq T'_{min}[°C.]$$

where $T'_{min}(c) = A + B \times (c/100) + C \times (c/100)^2 + D \times (c/100)^3$
and
$A = +68.759, B = +124.77, C = -12.851, D = -10.095,$ where c is the instantaneous $CH_2O$ content of the aqueous formaldehyde solution during the evaporation in percent by weight and is from 20 to 99% by weight.

Preference is given to using an aqueous formaldehyde solution having a $CH_2O$ content of from 50 to 99% by weight, particularly preferably from 70 to 95% by weight, in particular from 70 to 90% by weight, as starting material.

The $CH_2O$ content of the aqueous formaldehyde solution is the content of formaldehyde in free, monomeric form, in the form of methylene glycol or polyoxymethylene glycols, calculated as $CH_2O$.

The evaporation temperature is set by selection of the pressure during the evaporation process. This is selected so that the resulting evaporation temperature T(p) during the entire evaporation process in which the aqueous formaldehyde starting solution is partly or completely evaporated and the high-concentration gaseous formaldehyde is thus obtained remains above the limit value defined by the above formula. This limit value is concentration-dependent, with T(c) giving the dependence of this limit value on the instantaneous formaldehyde concentration of the aqueous formaldehyde solution at any point in time during the evaporation process. As can be seen from the above formula, the temperature limit value increases with the formaldehyde concentration. Thus, it can be necessary to increase the pressure during gradual concentration of the aqueous formaldehyde solution so as to prevent the temperature limit value from being exceeded.

In general, the pressure during the partial evaporation is in the range from 0.1 to 50 bar, preferably in the range from 0.5 to 17 bar.

The evaporation of the aqueous formaldehyde solution can be partial or complete and can be carried out continuously or batchwise.

If the evaporation is complete, the gas phase obtained has, overall, the same $CH_2O$ content as the liquid phase present at the beginning of the evaporation. Surprisingly, in the case of only partial evaporation too, the formaldehyde concentration, calculated as $CH_2O$, of the gas phase is close to or above the formaldehyde concentration, calculated as $CH_2O$, of the liquid phase. The system thus behaves in a manner similar to an azeotrope over a wide concentration range. This may be attributable to additional monomeric formaldehyde being formed continuously during the evaporation process by depolymerization of the polyoxymethylene glycols present in the solution, while water is continuously liberated by condensation of relatively short-chain polyoxymethylene glycols to form longer-chain polyoxymethylene glycols.

Gaseous formaldehyde/water mixtures in which the molar ratio of formaldehyde to water ($CH_2O:H_2O$) is $\geq 0.6$ are thus obtained. This ratio is preferably $\geq 1.4$, particularly preferably $\geq 1.6$.

The evaporation of the aqueous formaldehyde solution can be carried out in the presence of acidic or basic catalysts which catalyze the depolymerization and condensation reactions outlined above. However, for cost reasons and also to avoid deposits on the heat exchanger surfaces, the additions of catalyst should be kept small. Catalysis can be carried out homogeneously or heterogeneously in a suspension or fixed-bed mode.

The evaporation can be carried out in commercial apparatuses. Examples of suitable apparatuses are stirred vessels which can be heated, for example, by means of jackets or coiled tubes (internal or external). Apparatuses having heat exchanger characteristics, e.g. shell-and-tube heat exchangers, plate apparatuses or helically bound tubes, are particularly useful. These can be operated in cocurrent, countercurrent or cross-current. Heating can be carried out by means of any media, for example using condensing steam or by means of single-phase liquids or gases. Evaporation of the aqueous formaldehyde solution can be carried out in a single pass through the evaporator or with circulation. If, in particular, complete evaporation is sought, a single pass of the formaldehyde solution through the evaporator will generally not be sufficient.

The formaldehyde solution is evaporated at a temperature at which no solid precipitates. Preference is given to maintaining a temperature at which no solid precipitates at every point in the evaporator. For example, this temperature is maintained both in the evaporator itself and, when the evaporator is operated with circulation, in the circuit through which circulation occurs and, when the aqueous formaldehyde solution is taken off, in the facilities downstream of the evaporator.

For this purpose, a temperature which obeys the relationship $$T \geq T''_{min}$$

where $T''_{min}(c) = A' + B' \times (c/100) + C' \times (c/100)^2 + D' \times (c/100)^3$
and
$A' = +6.0156, B' = +52.918, C' = +49.699, D' = +34.286,$ where c is the instantaneous $CH_2O$ content of the aqueous formaldehyde solution during the evaporation in percent by weight and is from 20 to 99% by weight, is maintained in the aqueous formaldehyde solution at every point in the evaporator.

However, the evaporation temperature should not exceed an upper temperature limit value $T_{max}$ since decomposition of the gaseous formaldehyde into CO and hydrogen takes place at temperatures which are too high. This upper temperature limit value is generally 300° C., preferably 200° C.

The preparation of the high-concentration gaseous formaldehyde can also be carried out in a film evaporator or thin film evaporator. The preparation can also be carried out in a helical tube evaporator as described in DE-A 27 19 967. One suitable film evaporator is shown in FIG. 1. This is a thin film evaporator. The feed 1, consisting of raw solution (starting material mixture) and, if desired, a recycle stream, is firstly fed to a liquid distributor 2. This distributes the raw solution over an evaporation surface 3. The evaporation surface 3 (heat-exchange surface) usually has a cylindrical shape, but can also be at least partly conical. It is in thermal contact with the inside of a heating jacket 4 which supplies heat to the evaporation surface 3. The liquid distributor 2 contributes to the feed solution being uniformly distributed over the circumference of the evaporation surface 3.

Rotating wiper blades 5 then distribute the solution further over the evaporation surface 3, ensure maintenance and transport of a liquid film on the evaporation surface 3 and contribute to intensification of heat and mass transfer in the liquid. These wiper blades 5 are driven by a drive device 6. Depending on the configuration and positioning of the wiper blades 5, the liquid film can be kept thin or can be banked up. It is in this way possible to alter the residence time or the residence time distribution of the solution in the film evaporator. The typical residence time of the solution in the film evaporator is from 1 s to 10 min, preferably from 2 s to 2 min.

A heating medium, e.g. steam, is fed into the heating jacket through a heating medium inlet 7. This heating medium heats the evaporation surface. Cooled heating medium, e.g. condensed water in the case of steam as heating medium, is discharged via the heating medium outlet 8.

As a result of the supply of heat to the evaporation surface 3, part of the solution fed to the film evaporator is vaporized.

The vapor formed (i.e. vaporized liquid or gases) goes into a phase separation space 9 and from there into a droplet precipitator 10. Here, liquid droplets entrained in the vapor are removed from the gas phase and returned to the liquid (solution). The concentrate 13 is discharged in a suitable way from the phase separation space 9, while the vapor 12 is taken off from the droplet precipitator 10.

If an aqueous formaldehyde solution is introduced into the film evaporator described and is evaporated at a temperature $T<T'_{min}$, the liquid 13 becomes enriched in the polyoxymethylene glycols, while the condensate from the vapor 12 is low in polyoxymethylene glycols and rich in formaldehyde, methylene glycol and water. However, if the temperature is above the limit value $T'_{min}$ defined by the above formula, the gas phase has a formaldehyde content which comes very close to the formaldehyde content of the liquid phase.

In a particular embodiment, the condenser can be integrated into the body of the evaporator, which results in a shorter residence time of the vaporized components in the vapor phase and also a more compact construction.

Apart from the embodiment of a film evaporator shown in FIG. 1, it is also possible to use an apparatus without any mechanical influence on the liquid film present on the evaporation surface. The heat-transfer surface of such a falling film evaporator or falling stream evaporator can be configured as tubes or plates.

The process of the present invention preferably starts out from moderately concentrated or highly concentrated formaldehyde solutions having a $CH_2O$ content of from 50 to 99% by weight which have been stabilized against precipitation of solids as described below after they have been prepared.

Relatively highly concentrated formaldehyde solutions containing, for example, >70% by weight of $CH_2O$ are initially obtained as a single phase in the preparation at low temperatures of from about 20 to 50° C. However, precipitation of solids occurs after a certain time. The cause appears to be growth of the polyoxymethylene glycol chains in the formaldehyde solution until the solubility limit is exceeded. The solutions can be stabilized against precipitation of solids by heating them at a heating rate of at least 5° C./min to a temperature of from 80° C. to 200° C. immediately after they have been prepared and leaving them at a temperature in this range. "Immediately after they have been prepared" means that the high-concentration formaldehyde solution obtained at, for example, from 20 to 60° C. is heated at the specified heating rate after not more than 60 minutes, preferably after not more than 5 minutes.

The heating rate is preferably at least 10° C./min. A heating rate of at least 10° C./min is preferred particularly when the pH of the solution is <3 or >6. The solution is preferably heated at the specified heating rate to at least 100° C. and the temperature subsequently does not go below this value. The pH of the high-concentration formaldehyde solution is usually in the range from 1 to 10, preferably from 2 to 9, particularly preferably from 6 to 8. The pH can be brought into the desired range by addition of buffer substances, for example a formate buffer.

Stabilization and evaporation of the high-concentration aqueous formaldehyde solutions are preferably carried out in one apparatus at superatmospheric pressure.

The high-concentration gaseous formaldehyde obtained can be used for a large number of chemical reactions. Examples of such reactions are the reaction of acetylene with formaldehyde solution in a Reppe reaction to form butynediol which can be hydrogenated to give butanediol;

aldolization reactions of formaldehyde with itself or with higher aldehydes to form polyhydric alcohols and sugars, pentaerythritol, trimethylolpropane and neopentyl glycol;

the reaction of formaldehyde and CO to give glycolic acid;

the preparation of chelating substances such as glycol nitrites from solutions of formaldehyde;

the reaction of formaldehyde with olefins in a Prins reaction to give alpha-hydroxymethyl compounds;

condensation reactions of formaldehyde with amines such as aniline or toluidine to form Schiff bases which can react further to give diphenylmethane derivatives such as diphenylmethanediamine;

reaction of hydroxylamine with formaldehyde to form oximes;

reaction of formaldehyde with diols to form cyclic ethers, for example of glycol and formaldehyde to form dioxolane.

In a particularly preferred use, the gaseous formaldehyde/water mixture is passed to a trioxane or tetraoxane synthesis. Here, the gaseous mixture can be dewatered using methods known to those skilled in the art. The synthesis of trioxane is described, for example in AT 252913.

This listing is not exhaustive. Textbooks on organic chemistry and industrial chemistry give further examples of reactions. However, the listing is intended to illustrate, by way of example, the industrial importance of formaldehyde as a synthetic building block in the overall field of organic chemistry. The products obtained include both small tonnage intermediates in the pharmaceuticals or crop protection sectors, e.g. oximes, and large tonnage products such as diphenylmethane derivatives.

The invention is illustrated by the following example.

EXAMPLE

In a laboratory experiment, a high-concentration formaldehyde solution is prepared in a thin film evaporator as shown in FIG. 1 in a single pass. The evaporator has an evaporation area of 0.092 $m^2$ and a length of 1.1 m. A 48% strength by weight aqueous formalin solution is introduced at the top. The flow rate is 615 g/h. The wall temperature is 90° C. and the pressure is 80 mbar. At the bottom, 298 g/h of a high-concentration formaldehyde solution having a concentration of 84% by weight are taken off. 321 g/h of vapor are taken off at the top.

The solution from the bottom is conveyed by means of a laboratory pump into a heated standard laboratory stirred reactor having a capacity of 1 l. The reactor is maintained at an internal temperature of 155-160° C., with a pressure of about 8 bar being established. A liquid stream of 27 g/h is taken off from the reactor. A gas stream of 268 g/h is taken off from the gas phase of the reactor. According to analysis, this stream contains from 82 to 85% by weight of formaldehyde, calculated as $CH_2O$.

We claim:

1. A process for preparing high-concentration gaseous formaldehyde having a molar $CH_2O:H_2O$ ratio of $\geq 0.6$ from an aqueous formaldehyde solution by evaporation of at least part of the solution, in which the aqueous formaldehyde solution is heated to a evaporation temperature T and the gas phase formed is taken off, wherein the evaporation temperature T obeys the relationship:

$$T\,[°\mathrm{C.}] \geq T'_{min}[°\mathrm{C.}]$$

where $T'_{min}(c)=A+B\times(c/100)+C\times(c/100)^2+D\times(c/100)^3$
and
$A=+68.759, B=+124.77, C=-12.851, D=-10.095$,
where c is the instantaneous $CH_2O$ content of the aqueous formaldehyde solution during the evaporation in percent by weight and is from 20 to 99% by weight.

2. A process as claimed in claim 1, wherein the aqueous formaldehyde solution used as starting material in the process has $CH_2O$ content of from 50 to 99% by weight.

3. A process as claimed in claim 2, wherein the aqueous formaldehyde solution has $CH_2O$ content of from 70 to 90% by weight.

4. A process as claimed in claim 1, wherein the pressure during the evaporation is from 0.1 to 50 bar.

5. A process as claimed in claim 1, wherein the molar $CH_2O:H_2O$ ratio is $\geq 1.4$.

6. A process as claimed in claim 1, wherein a temperature which obeys the relationship $$T\,[°\mathrm{C.}] T''_{min}[°\mathrm{C.}]$$

where $T''_{min}(c)=A'+B'\times(c/100)+C'\times(c/100)^2+D'\times(c/100)^3$
and
$A'=+6.0156, B\alpha=+52.918, C'=+49.699, D'=+34.286$,
where c is the instantaneous $CH_2O$ content of the aqueous formaldehyde solution during the evaporation in percent by weight and is from 20 to 99% by weight, is maintained in the aqueous formaldehyde solution at every point in the evaporator.

7. A process as claimed in claim 1, wherein the evaporation is carried out in a stirred vessel, a helical tube, a film evaporator or another apparatus having heat exchanger characteristics.

8. A process as claimed in claim 1, wherein the aqueous formaldehyde solution used as starting material in the process is prepared by oxidative dehydrogenation of methanol.

9. A process for preparing high-concentration gaseous formaldehyde having a molar $CH_2O:H_2O$ ratio of $\geq 0.6$ from an aqueous formaldehyde solution by evaporation of at least part of the solution, in which the aqueous formaldehyde solution is heated to a evaporation temperature T and the gas phase formed is taken off, wherein the evaporation temperature T obeys the relationship:

$$T\,[°\mathrm{C.}] \geq T'_{min}[°\mathrm{C.}]$$

where $T'_{min}(c)=A+B\times(c/100)+C\times(c/100)^2+D\times(c/100)^3$
and
$A=+68.759, B=+124.77, C=-12.851, D=-10.095$,
where c is the instantaneous $CH_2O$ content of the aqueous formaldehyde solution during the evaporation in percent by weight and is from 20 to 99% by weight and wherein the aqueous formaldehyde solution used as starting material in the process has $CH_2O$ content of from 50 to 99% by weight.

10. A process as claimed in claim 9, wherein the aqueous formaldehyde solution used as starting material has $CH_2O$ content of from 70 to 90% by weight.

11. A process as claimed in claim 10, wherein the pressure during the evaporation is from 0.1 to 50 bar.

12. A process as claimed in claim 11, wherein the molar $CH_2O:H_2O$ ratio is $\geq 1.4$.

13. A process as claimed in claim 12, wherein a temperature which obeys the relationship $$T\,[°\mathrm{C.}] \geq T''_{min}[°\mathrm{C.}]$$

where $T''_{min}(c)A'+B'\times(c/100)+C'\times(c/100)^2+D'+(c/100)^3$
and
$A'=+6.0156, B'=+52.918, C'=+49.699, D'+34.286$,
where c is the instantaneous $CH_2O$ content of the aqueous formaldehyde solution during the evaporation in percent by weight and is from 20 to 99% by weight, is maintained in the aqueous formaldehyde solution at every point in the evaporator.

14. A process as claimed in claim 13, wherein the evaporation is carried out in a stirred vessel, a helical tube, a film evaporator or another apparatus having heat exchanger characteristics.

15. A process as claimed in claim 14, wherein the aqueous formaldehyde solution used as starting material in the process is prepared by oxidative dehydrogenation of methanol.

* * * * *